(12) United States Patent
Burren et al.

(10) Patent No.: US 7,811,263 B2
(45) Date of Patent: Oct. 12, 2010

(54) DOSE METERING MECHANISM FOR AN INJECTION DEVICE

(75) Inventors: Stefan Burren, Bremgarten (CH); Ulrich Moser, Heimiswil (CH); Christian Schrul, Utzenstorf (CH)

(73) Assignee: TecPharma Licensing AG, Burgdorf (CH)

( * ) Notice: Subject to any disclaimer, the term of this patent is extended or adjusted under 35 U.S.C. 154(b) by 374 days.

(21) Appl. No.: 11/439,389

(22) Filed: May 23, 2006

(65) Prior Publication Data

US 2007/0016142 A1    Jan. 18, 2007

(30) Foreign Application Priority Data

May 24, 2005    (DE) .................. 10 2005 023 854

(51) Int. Cl.
*A61M 5/00*    (2006.01)
(52) U.S. Cl. ...................... 604/211; 604/207
(58) Field of Classification Search .......... 604/207–211
See application file for complete search history.

(56) References Cited

U.S. PATENT DOCUMENTS

| 5,957,896 | A | * | 9/1999 | Bendek et al. ............... 604/207 |
| 6,086,567 | A | * | 7/2000 | Kirchhofer et al. .......... 604/211 |
| 6,221,053 | B1 | * | 4/2001 | Walters et al. ............... 604/211 |
| 6,899,699 | B2 | * | 5/2005 | Enggaard ..................... 604/246 |
| 7,377,913 | B2 | * | 5/2008 | Gurtner ....................... 604/211 |
| 2004/0260247 | A1 | * | 12/2004 | Veasey et al. ................ 604/207 |

FOREIGN PATENT DOCUMENTS

WO    WO 97/36626    10/1997

\* cited by examiner

*Primary Examiner*—Nicholas D Lucchesi
*Assistant Examiner*—Rebecca E Eisenberg
(74) *Attorney, Agent, or Firm*—Dorsey & Whitney LLP; David E. Bruhn, Esq.

(57) ABSTRACT

A dose metering mechanism for setting a dose to be administered from an injection device, the mechanism including a setting sleeve marked with dose amounts by which a dose to be administered is set by rotation, and a rotating sleeve which can be rotated out of the dose metering mechanism to prime the dispensing of a dose and is marked with dose amounts, the setting sleeve coupled to the rotating sleeve whereby when the rotating sleeve is fully rotated out, the dose amount of the setting sleeve is not offset from an associated dose amount of the rotating sleeve.

16 Claims, 8 Drawing Sheets

DOSE METERING MECHANISM FOR AN INJECTION DEVICE

CROSS-REFERENCE TO RELATED APPLICATION

This application claims the benefit of German Application No. 10 2005 023 854.8, filed May 24, 2005, the contents of which are incorporated in its entirety by reference herein.

BACKGROUND

The present invention relates to devices for dispensing, injecting or delivering substances, and to methods of making and using such devices. More particularly, it relates to a dose-metering mechanism for an injection device, including a metering mechanism by means of which a dose or quantity of a substance to be dispensed from or with the aid of the injection device can be set.

Document DE 202 09 051 U1 discloses an injection device with a dose-setting element blocked in an end position and the injection device has a dose-setting element which, in order to select the product dose, is able to effect a rotating movement relative to the housing in a first direction of rotation as far as an end position and in an opposite direction of rotation, and is coupled with a drive mechanism, by means of which a selected product dose is dispensed from a reservoir, so that the drive mechanism dispenses the product dose selected by the dose-setting element when operated. An anti-rotation lock prevents the dose-setting element from rotating beyond an end position in the first direction of rotation.

Patent specification EP 0 828 527 B1 discloses an injection device with a longitudinally displaceable driving sleeve, provided with printed doses so that a reading can be taken of the dose to be injected and a mechanism which prevents the injection device from being loaded when a push rod is pulled out if the supply of an ampoule has completely run out, and the dose-metering device provides a reading on a dose scale disposed in the region of a top end of the driving sleeve indicating an actual possible dose which can be administered.

German patent application No. 10 2005 001 159.4 discloses a dose-metering device for an injection device with a multiplication ratio, which in particular enables a small dose quantity to be set exactly and dispensed.

Patent specification WO 2004/078239 A1 discloses a device for administering medicaments with a housing incorporating an internal thread, a dose selection sleeve with a thread which engages in the internal thread of the housing, a rotating sleeve which is releasably connected to the dose selection sleeve, and a coupling disposed between the dose selection sleeve and the rotating sleeve, and the two sleeves are able to rotate relative to the housing when the dose selection sleeve and the rotating sleeve are coupled. When the dose selection sleeve and the rotating sleeve are uncoupled, the dose selection sleeve is able to rotate relative to the housing, whereas the rotating sleeve is prevented from rotating relative to the housing, thereby permitting an axial movement of the rotating sleeve so that a force is transmitted in the longitudinal direction to the proximal end of the medicament administering device.

SUMMARY

An object of the present invention is to provide a dose metering mechanism for setting and/or dispensing a dose to be dispensed from an injection device, as well as an injection device incorporating such a dose metering mechanism, and a method by means of which the dose can be reliably set, reducing the risk of incorrect use when setting and/or dispensing the dose.

In one embodiment, the present invention comprises a dose metering mechanism for setting a dose of a medicinal substance such as insulin or hormones, for example, contained in the injection device or an ampoule, to be dispensed from an injection device, which dose metering mechanism may be provided on an injection device or as part of it, and has a setting sleeve, provided at the rear end of the injection device, which is able to rotate about the longitudinal axis of the device and has one or more marks or markings in the circumferential direction which specify the quantity of a substance to be dispensed from the injection device in the respective set position or the quantity of an active ingredient contained in the substance that will be dispensed with a dose of the substance. By rotating the setting sleeve, a user can turn to a marking provided on the setting sleeve as far as a point indicated on the injection device by an arrow or other suitable indicator to set the quantity of substance or active ingredient which should be dispensed from the injection device during a subsequent dispensing procedure. The dose metering mechanism also has a rotating sleeve, which is able to rotate out of the dose metering mechanism or injection device in order to prime a dose dispensing procedure, relative to a housing of the injection device or relative to the setting sleeve, and one or more markings are provided on the rotating sleeve extending round its external face in the circumferential direction. These markings may be identical to the markings provided on the setting sleeve in terms of their value or can be matched with them. For the purpose of the invention, the rotating sleeve is coupled with the setting sleeve, for example directly by a thread-type engagement or indirectly by means of an intermediate element, so that when the rotating sleeve is in the fully extracted state or pulled out to the maximum, as determined by the setting or rotational position of the setting sleeve, it is positioned in such a way relative to the setting sleeve that a marking provided on the rotating sleeve is not offset from the associated marking of the setting sleeve in the circumferential direction. In other words, the mark lies in an axial extension of the marking on the rotating sleeve, so that dose marking of a dose display on the rotating sleeve lie in an axial line with the corresponding dose display or marking of the setting sleeve when the rotating sleeve is in the fully extracted state whenever a dose is being set by means of the setting sleeve. As a result the dose is simultaneously set on one side of the pen, and a simple check can be made on the same side of the pen to ascertain whether the correct dose has been primed by ensuring that the relevant markings provided on the setting sleeve and the rotating lie adjacent to one another. If this is not the case, the user can easily see that the set dose was not primed and should not, therefore, be dispensed.

In some embodiments, the setting sleeve may be coupled with the rotating sleeve by means of a thread engagement, for example, in which case the rotating sleeve is coaxially guided in the setting sleeve which has an internal thread in which an external thread of the rotating sleeve engages. The setting sleeve and rotating sleeve can also be uncoupled, i.e., the setting sleeve is rotatably mounted on the injection device, with which the rotating sleeve engages by means of a thread or other suitable connection. This being the case, a stop element, such as a web, a stop strip or the like, may be provided on the setting sleeve, disposed in the axial direction, in other words more or less parallel with the mid-axis of the injection device, to permit a 360° rotation of the rotating sleeve. Alternatively, it could extend round the internal face of the setting sleeve, e.g., in the form of a thread or threaded portion, to permit a rotation of the setting rotating sleeve up to 720°.

In some embodiments, a counter-stop may be provided on the rotating sleeve, such as a stop element projecting out from the external face of the rotating sleeve, to provide a radial stop restriction. In this case, the sleeve can be rotated in the setting sleeve until the counter-stop element of the rotating sleeve lies against the stop of the setting sleeve, thereby preventing any further rotation of the rotating sleeve relative to the setting sleeve, which enables the injection device to be primed as far as a position fixed by a rotation position of the setting sleeve prior to administering a dose. The stop element of the rotating sleeve is able to restrict the maximum setting rotation of the setting sleeve to approximately 360° or 720°, for example. An axial or coil-shaped or helical stop element may also be provided on the rotating sleeve, which co-operates with one or more counter-stop elements of the setting sleeve.

The marking or markings on the setting sleeve may be circumferentially disposed, e.g., without an axial offset or, in an alternative arrangement, with an alternating axial offset, so that the markings 0.2, 0.4, 0.6, . . . extend radially around the setting sleeve and the markings 0.1, 0.3, 0.5, . . . may be disposed lying in between, axially offset. Like those on the setting sleeve, the markings on the rotating sleeve may also be stepped or staggered, i.e., in addition to being offset in the circumferential direction, markings which have a higher value may also be offset in the distal or proximal direction so that when the rotating sleeve is turned and moved out of the setting sleeve, the marking value relating to the respective quantity set and primed is always totally legible once the setting sleeve has been rotated out far enough for the dose assigned to this marking to be administered when the rotating sleeve is pushed in and turned in or inserted. Accordingly, markings relating to a higher value will still be fully legible.

A reading can be taking from the markings on the rotating sleeve, indicating whether a dose set by means of the setting sleeve has been correctly primed or, if the dose metering mechanism contains a restriction mechanism, which will be described below, whether the dose set by means of the setting sleeve is still available and can be administered, thereby enabling a user to ascertain whether a dose can still be or can no longer be administered from the injection device.

In some embodiments, the present invention comprises a method of priming the dispensing of a dose of a substance to be administered from an injection device, whereby a setting element, in particular a setting sleeve, is used to set the quantity of the dose to be administered by turning the setting element, and the dispensing of the substance is primed by means of a priming element, in particular a rotating sleeve, by rotating out the priming element, and by means of a mechanical coupling between the setting element and priming element, once the dose has been set, the priming element can be rotated out as far as a stop until a marking disposed on the priming element defining a specified dose is disposed in the axial extension of an associated set dose marking on the setting element.

In some embodiments, the present invention comprises a method of priming the dispensing of a dose of a substance to be administered from an injection device, whereby, by means of a setting element, in particular a setting sleeve, the quantity of the dose to be administered is set by rotating the setting element, and dispensing of the substance is primed by means of a priming element, in particular a rotating sleeve, by rotating out the priming element, and a locking element which is moved in the direction towards an end position, in particular an end stop, with every priming procedure restricts the outward rotating movement of the priming element if the quantity of substance available for dispensing is less than the quantity of the dose to be administered set by means of the setting element.

In some embodiments, the present invention comprises a dose metering mechanism for setting a dose to be administered from an injection device by means of a setting sleeve which can be displaced, for example rotated, relative to the dose metering mechanism or relative to an injection device connected to or coupled with it, to set a quantity or dose of a substance to be administered from the injection device. To prime the dispensing of a dose, a rotating sleeve is coupled with the setting sleeve and can be rotated out of or screwed out of the dose metering mechanism or injection device in order to prime the injection device, i.e., to prepare the dispensing of a substance, which is administered by turning the rotating sleeve back in again or inserting it in the dose metering mechanism or injection device. For the purpose of the invention, in some embodiments, a rotation-restricting element is disposed on the setting sleeve or is coupled with it. In some embodiments, this element may be a radial stop in the form of a web or strip extending in the axial direction or in a spiral, the rotation position of which can be varied relative to the injection device by means of a setting or rotating movement of the setting sleeve. Provided on or coupled with the rotating sleeve is a counter-stop, as a result of which the rotating sleeve can only be rotated out of the setting sleeve or injection device until the rotating movement of the rotating sleeve is restricted by a contact of the stop of the setting sleeve with the counter-stop of the rotating sleeve. Accordingly, depending on the design of the stop and counter-stop elements, a maximum rotation angle of the rotating sleeve for priming the dispensing of a substance, can be fixed at 360° if using an axially extending outer element permitting a full rotation, for example, or 720° if using a stop element permitting two rotations for example. In some embodiments, a dose is set by means of the setting sleeve irrespective of an outward rotating movement of the rotating sleeve, i.e., once a dose has been set by means of the setting sleeve, repeated dispensing from the injection device can take place without another setting routine if the rotating sleeve is always rotated out as far as the stop and is then rotated or pushed back inwards in order to administer the substance. The process of setting the dose is therefore uncoupled from the process of priming the injection device and can be undertaken by a doctor who can lock the setting sleeve in the setting position relative to the injection device by means of a locking element which may optionally be provided, thereby making it impossible for a user to administer too high a dose from the injection device. By simply rotating the rotating sleeve out as far as a radial stop position pre-set by means of the setting sleeve, the injection device will always be correctly primed by the user. This enables a "dose memory" to be set up, and as a result it is not necessary for a separate coupling movement to couple and uncouple the setting and rotating sleeves.

In some embodiments, the stop may be provided on the internal face of the setting sleeve in the form of a radial stop, for example as a circumferentially extending web running in the axial direction or alternatively in a spiral pattern on the internal face, the rotation position of which can be varied by a rotation of the setting sleeve relative to the injection device. The counter-stop may be provided in the form of a web or cam projecting radially out from the rotating sleeve, which stands far enough outwardly of the external face of the rotating sleeve for the projecting cam to lie in contact with the stop of the setting sleeve after a pre-defined rotation angle when the rotating sleeve is rotated, guided in a thread of the injection device, thereby preventing the rotating sleeve from being turned any further.

As mentioned above, in some embodiments, the setting sleeve may have a locking or fixing element, by which the setting position of the setting sleeve can be fixed or locked relative to the injection device. Likewise, another option would be for the setting sleeve to be rotated relative to the injection device or a housing only if the rotating sleeve is in a pre-defined positional relationship relative thereto, in other words completely pushed in, for example. To this end, a circumferentially extending cut-out, groove or recess may be provided on the rotating sleeve, which does not lie opposite one or more latching cams of the setting sleeve unless the rotating sleeve is in the fully pushed-in state, and these may engage in catch orifices provided on the internal face of an injection housing or another element, thereby preventing the setting sleeve from rotating relative to the injection device or to the housing of the injection device. Only if a peripherally extending groove lies opposite one of the catch elements of the rotating sleeve, guided in the setting sleeve, can these be released and moved out of an engagement in which the rotation position of the setting sleeve is locked, so that the setting sleeve can be rotated in order to set a dose. When the rotating sleeve is rotated out of the setting sleeve, in other words is displaced relative thereto in the axial direction for example, the peripherally extending groove of the rotating sleeve no longer lies opposite the catch elements of the setting sleeve where they engage in co-operating complementary catch elements or catches of the injection device and prevent a rotation of the setting sleeve relative to the injection device or a housing thereof.

In some embodiments, the present invention relates to a dose metering mechanism for setting a dose to be administered from the injection device by means of a setting sleeve used to set the dose, e.g., by rotating the setting sleeve relative to the injection device, whereby the setting sleeve can not be axially varied relative to the injection device, in other words is not extracted from it or pushed into it. In some embodiments, a rotating sleeve co-operates or is coupled with the setting sleeve in such a way that it is not proximally extracted when a dose is being set but can be extracted from the injection device or from the housing irrespective of the setting procedure once the dose has been set to prime the injection device. This helps ensure that the setting procedure can be uncoupled from the process of priming the injection device or is independent of it, so that an incorrect dose or overdose can not occur when priming the injection device.

In some embodiments, the invention comprises a method of setting a dose to be administered from an injection device, whereby the dose to be administered can be set by means of a setting element, in particular a dose-setting means, and the injection device can then be primed by means of a priming element, in particular a rotating sleeve, to dispense the set dose from the injection device in a subsequent step, and the setting procedure is uncoupled from the priming procedure.

In some embodiments, the present invention comprises a dose metering mechanism for setting a dose to be administered from the injection device by means of a rotating sleeve, which can be rotated out of the injection device to prime the injection device and has an internal thread. A threaded rod is guided in the rotating sleeve and can be displaced relative to the rotating sleeve. A locking element with an external thread is mounted on the threaded rod so that it can slide and is prevented from rotating, and can engage in the internal thread of the rotating sleeve, and can be screwed forwards or screwed in as far as a front or distal stop element of the rotating sleeve to restrict the priming movement of the rotating sleeve in the fully screwed-forward state. If the threaded rod is mounted so that it is prevented from rotating in the injection device during a priming procedure by means of a first anti-rotation or back-rotation lock, and if the thread turns are designed accordingly, in other words if the external thread of the locking element engaging in the internal thread of the rotating sleeve extends in the same direction as the external thread of the rotating sleeve screwed into the injection device, when the rotating sleeve is rotated out of the injection device, the locking element is screwed in the distal direction relative to the rotating sleeve during the process of rotating the rotating sleeve out of the injection device in the proximal direction. When the rotating sleeve is screwed back into the injection device, the relative position between the locking element and rotating sleeve remains unchanged when the threaded rod rotates in conjunction with the rotating sleeve, which can be achieved by means of a second anti-rotation or back-rotation lock, which may be provided on the rotating sleeve or connected to it. Due to the fact that the locking element is screwed into the rotating sleeve in the distal direction when the rotating sleeve is being primed, it is possible to ascertain the total quantity of a substance which can be administered from the injection device by means of the dose metering mechanism before the locking element has been fully screwed into the rotating sleeve or has reached a stop position, which prevents the rotating sleeve from being extracted further if the rotating sleeve is mounted so that it can not rotate on the threaded rod and is held locked in the injection device during the priming procedure by means of a first anti-rotation lock. Consequently, based on the last dose set, the locking element is able to block the rotating sleeve and hence settings above the quantity of substance which is still available for dispensing.

If the initial or starting position of the locking element on the threaded rod or in the rotating sleeve is fixed so that the priming routine needed for the distal inward rotation of the locking element as far as a stop does not exceed or corresponds to the relevant quantity of substance contained in the injection device, this will help ensure that a dose can not be primed which can no longer be administered from the injection device. Consequently, this will help prevent incorrect dosages when the last dose is administered from the injection device and a user will be able to tell, for example from the maximum last priming position blocked by the locking element, what quantity of substance he can still administer from the injection device so that he can decide not to use the injection device any longer, or can decide to administer the remaining quantity of the substance to be administered from the injection device, and then administer the remaining quantity needed for a treatment from another injection device or another ampoule.

In some embodiments, the thread of the threaded rod and the external thread of the locking element run or extend in the same direction.

A description will be given herein below of an anti-rotation or back-rotation lock which enables the threaded rod to be rotated in one direction relative to the injection device or relative to the rotating sleeve and blocks a rotation in the opposite direction. The anti-rotation locks on the injection device and on the rotating sleeve may be of the same design and have the same operating mechanism or principle as a ratchet.

In some embodiments, the present invention relates to a method of limiting a maximum possible dose or set quantity of an injection device, whereby a locking element is moved in the direction towards a stop or a locking or blocking position when the injection device is being primed prior to a dispensing procedure, and the maximum quantity of the substance to be primed a dose metering mechanism or administered from the injection device is set depending on the distance of the locking element from the locking or blocking position.

In some embodiments, the present invention comprises a threaded rod, which is able to exert pressure on a plug in a reservoir of an injection device containing a substance to be administered, and to a dose metering mechanism for setting a dose or substance to be administered from the injection device incorporating such a threaded rod.

In some embodiments, the injection device has a rotating sleeve, by means of which a dose to be administered form the injection device can be primed or set by turning the rotating sleeve, in other words by screwing the rotating sleeve out of or into the injection device. On its external face, the threaded rod has a thread, which may be provided in the form of a circumferentially extending thread or may comprise several threaded portions which are offset axially and/or in the circumferential direction, and is guided in the injection device and/or the setting sleeve and is axially displaceable therein, for example by means of a rotation-restricting element provided on the internal face of the injection device or setting sleeve. The thread of the threaded rod may protrude from the latter, for example may be provided in the form of a web, or may be recessed in the form of a groove or the like.

In some embodiments, a rotation-restricting element may be provided on the injection device, setting sleeve and/or rotating sleeve. The rotation-restricting element may be fixedly joined to the housing of the injection device, for example, and may be provided in the form of an anti-rotation catch, anti-rotation lock or back-rotation lock. A rotation-restricting element within the meaning of the invention is an element which, in co-operation with an element guided by or in the rotation-restricting element, such as the threaded rod for example, permits a rotation in one direction only and blocks or prevents rotation in the opposite direction. To this end, the threaded rod may be provided with appropriate counter-elements. For example, a rotation-restricting systems may be achieved which operates on the principle of a known ratchet system, using a combination of catch lugs or cams on the rotation-restricting element or threaded rod, which engage in co-operating catch systems of the threaded rod or rotation-restricting element, such as a catch mechanism or teeth. For example, a catch lug may be provided on an elastic element biased in the radial direction, for example, a catch arm, which is disposed in the circumferential direction of the guided element, disposed on the latter or on the rotation-restricting element, or may be provided directly on the respective element without an elastic element and may have an angled portion on one face enabling a sliding movement out of an engaged position, and a non-angled face lying opposite the angled face which prevents a rotation in the direction opposite that needed to slide the catch element out.

In some embodiments, the thread provided on the threaded rod may have teeth on the thread or threaded portion, for example, in which one or more catch elements of one or more rotation-restricting elements can engage to permit a rotation of the threaded rod in one direction only relative to the rotation-restricting element. A threaded rod may therefore only be screwed into or only screwed out of a setting sleeve connected to a rotation-restricting element, in which case a movement in the opposite direction is blocked by the rotation-restricting element.

Like the rotating sleeve, in some embodiments, the injection device also has a rotation-restricting element, which permits a rotation of a threaded rod in the same direction and blocks it in the opposite direction. Since the rotating sleeve is mounted in the injection device so as to be rotatable, e.g., guided by a thread, and can be pulled out or screwed out of the injection device in order to prime it and pushed back in or screwed back into it in order to dispense a dose, a back-rotation lock provided on the rotating sleeve enables the threaded rod to be retained by the anti-rotation lock of the injection device as the rotating sleeve is being rotated out of the injection device, whereas the anti-rotation lock of the rotating device permits an outward rotating movement out of the injection device. When the rotating sleeve is screwed back into the injection device, the rotation-restricting element of the rotating sleeve engages in the threaded rod, causing the rotating sleeve to transmit the movement effected when screwing into the injection device to be transmitted to the threaded rod, driving the latter with it, thereby enabling the threaded rod to be rotated as well, due to the rotation restricting element of the injection device which blocked a rotation of the threaded device during the process of screwing the rotating sleeve out of the injection device.

Since the threaded rod is also rotated as the rotating sleeve is rotated inwards, the threaded rod, guided in a thread of the injection device for example, can be displaced distally in the injection device in order to push a plug or the like by a defined distance into a container, such as an ampoule, thus forcing out a fluid or a substance contained in the container to administer it through a dispensing orifice of the container to a patient.

In some embodiments, a rotating knob may be provided on the rotating sleeve, which can be rotated relative to the rotating sleeve so that a user can pull or screw the rotating sleeve out of the injection device, for example by pulling on the rotating knob, without the rotating knob rotating relative to the injection device, so that the rotating sleeve is retained so that it is rotatable in the rotating knob. The rotating sleeve can likewise be pushed in or turned or screwed into the injection device by pressing on the rotating knob without the rotating knob moving relative to the injection device.

DETAILED DESCRIPTION OF THE DRAWINGS

The injection device 1 has a housing or housing element 1a, in which a setting sleeve 2 is rotatably mounted as a means of making a one-off initial measurement or setting the injection device, e.g. by a doctor, or alternatively for setting different dosage quantities several times. Rotatably mounted inside the setting sleeve 2 is a rotating sleeve 3 with an external thread 3c which engages in an internal thread 1b of the injection device 1 or a housing part 1a of the injection device. The rotating sleeve 3 has an internal thread 3d, in which an external thread 5a of a locking element 5 engages, so that the rotating sleeve 3 is disposed in a thread engagement with the injection device 1 or a housing 1a thereof and in a thread engagement with the locking element 5. The locking element 5 is mounted so that it can not rotate but is axially displaceable on a threaded rod 4 and has two oppositely lying guide elements 5b, which engage in a guide groove 4a extending in the axial direction along the threaded rod 4 so that a rotation of the threaded rod 4 is always transmitted to the locking element 5, which rotates with the threaded rod 4 and which can also block a rotation of the threaded rod 4, for example when it is completely screwed into the rotating sleeve 3.

Figure 1A:
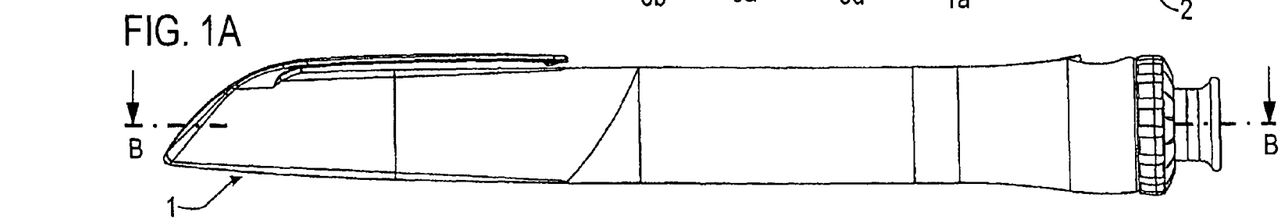
FIG. 1A is a side view of an embodiment of an injection device in accordance with the present invention.
Figure 1B:
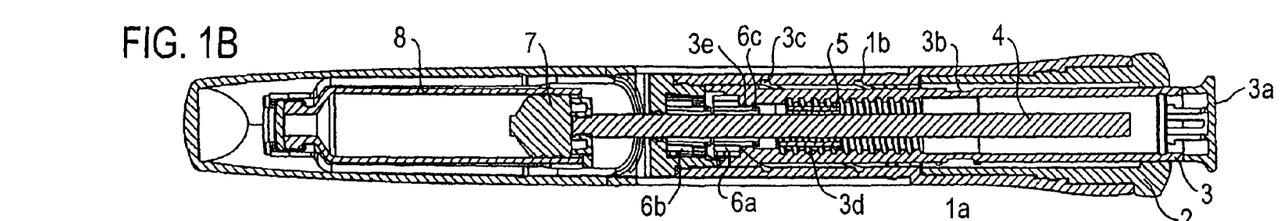
FIG. 1B is a side view along line B-B indicated in FIG. 1A.
Figure 1C:
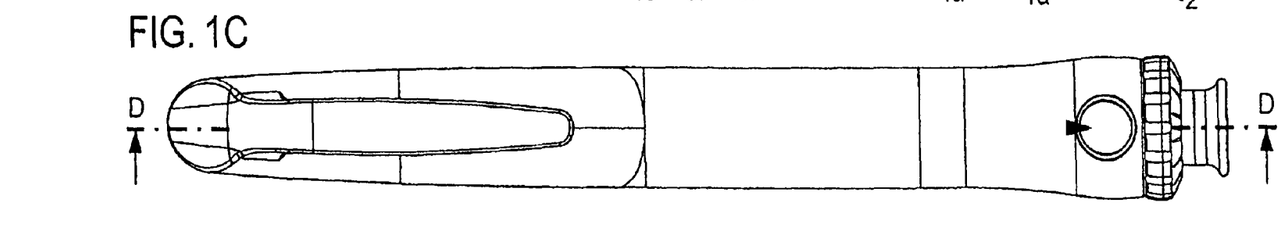
FIG. 1C is a plan view of the injection device illustrated in FIG. 1A.
Figure 1D:
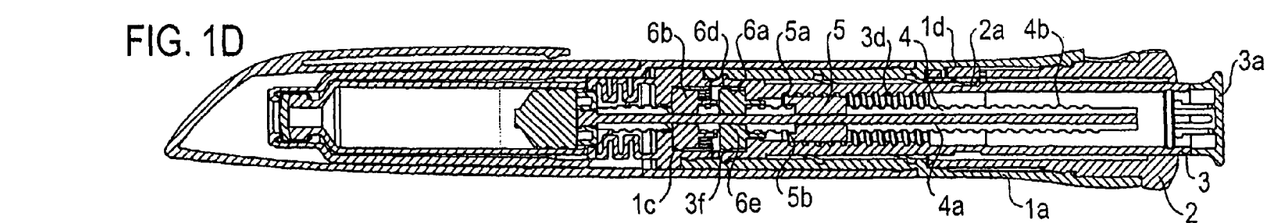
FIG. 1D is a view in section along line D-D indicated in FIG. 1C.

Provided at the distal end of the rotating sleeve 3 is a rotation-restricting element 6a, which is connected to the rotating sleeve 3 so that the rotation-restricting element 6a can not be released from the rotating sleeve 3 in the axial direction, and the rotation-restricting element 6a is retained by a drive 3e of the rotating sleeve 3 by means of catches or retaining elements 6c in such a way that although the rotation-restricting element 6e is mounted so that it can rotate relative to the rotating sleeve 3, it can not be displaced in the axial direction relative to the rotating sleeve 3.

The rotation-restricting element 6a has catch elements 6d biased radially outwards by means of resilient arms, which engage in teeth or a catch mechanism 3f extending circumferentially around the internal face of the distal end of the rotating sleeve 3, and the teeth 3f and the catch elements 6d are designed so that a rotation of the rotation-restricting element 6a in the rotating sleeve 3 is possible only in a direction in which the catch elements 6d are able to slide out of engagement with the teeth 3f, whereas a rotation in the opposite direction is prevented due to an appropriate design of the catch elements 6d which engage in the teeth 3f and block movement in the opposite direction, thereby making use of the one-sided rotation-restricting effect of a ratchet mechanism which is known per se.

Like the locking element 5, the rotation-restricting element 6a has guide elements 6e lying opposite one another, which engage in the axial guide or groove 4a of the threaded rod 4 and are thus prevented from rotating relative to the threaded rod 4, although the threaded rod 4 can be displaced axially relative to the rotation-restricting element 6a.

Another rotation-restricting element 6b of an identical construction to that of the rotation-restricting element 6a is mounted in the injection device 1 so that it can rotate and engages by mean of catch elements 6d in teeth 1c extending around the internal face of an injection device part so that the rotation-restricting element 6b can not be displaced in the axial direction in the injection device 1 and can rotate in only one direction of the injection device 1 and is prevented from rotating in the opposite direction.

Figure 2A:
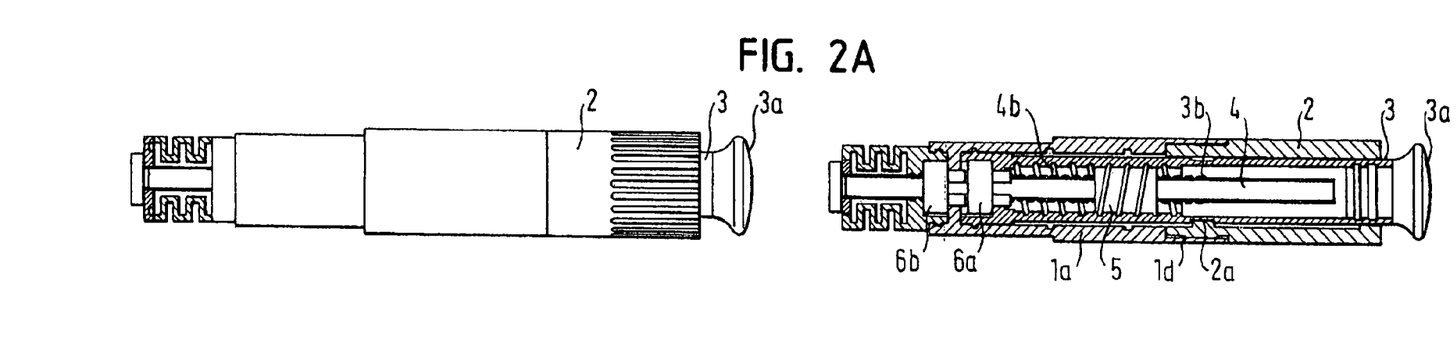
FIGS. 2A-2H illustrate positions of a dose metering mechanism when setting a dose, priming an injection device and administering a dose.

The operating principle of an embodiment of an injection device proposed by the invention will be explained with reference to FIGS. 2A-2H, which illustrate the different states of an embodiment of a dose metering mechanism in accordance with the present invention. FIG. 2A is a plan view showing a cross-section of a dose metering mechanism with a threaded rod 4, which is of a flattened design in the embodiment illustrated and is more or less rectangular in cross-section, and has threaded segments 4b on two oppositely lying side faces between which part sections of the threaded rod 4 with no thread elements lie. The threaded rod 4 is mounted in the locking element 5 or rotation-restricting elements 6a, 6d so that it can not rotate due to the fact that these elements are provided with orifices more or less matching the cross-sectional shape of the threaded rod 4.

A desired dose to be primed and administered is set by rotating the setting sleeve 2. The setting lock cam 2a of the setting sleeve 2 extends freely towards the inside and can be pushed into the release groove 3b in order to release the coupling of the setting sleeve 2 with the housing 1a obtained by the setting lock cam 2a engaging in catches lying on the internal face of the housing 1a.

Figure 2B:
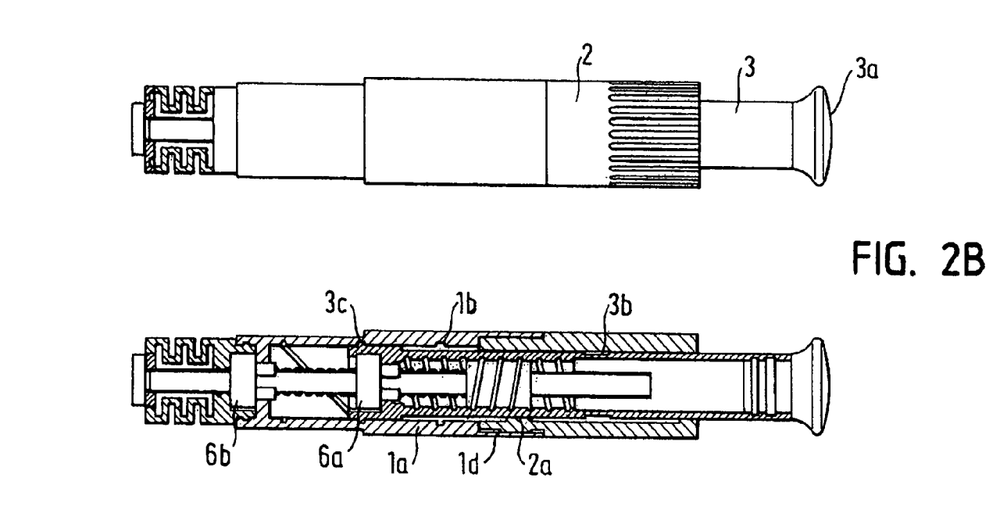

Once the dose has been set by means of the freely rotatable setting sleeve 2, the injection device is primed, as may be seen from the plan view and cross-sectional view illustrated in FIG. 2B. By pulling on the freely rotatable rotating knob 3a, the injection device is primed or loaded with the dose of 2.6 units, for example, set beforehand by means of the setting sleeve 2. The rotating sleeve 3 is pulled in the proximal direction (towards the right in FIG. 2B) by means of the freely rotatable rotating knob 3a and rotates due to the thread engagement of the external thread 3c of the rotating sleeve 3 in the internal thread 1c of the injection device housing 1a.

Figure 2C:
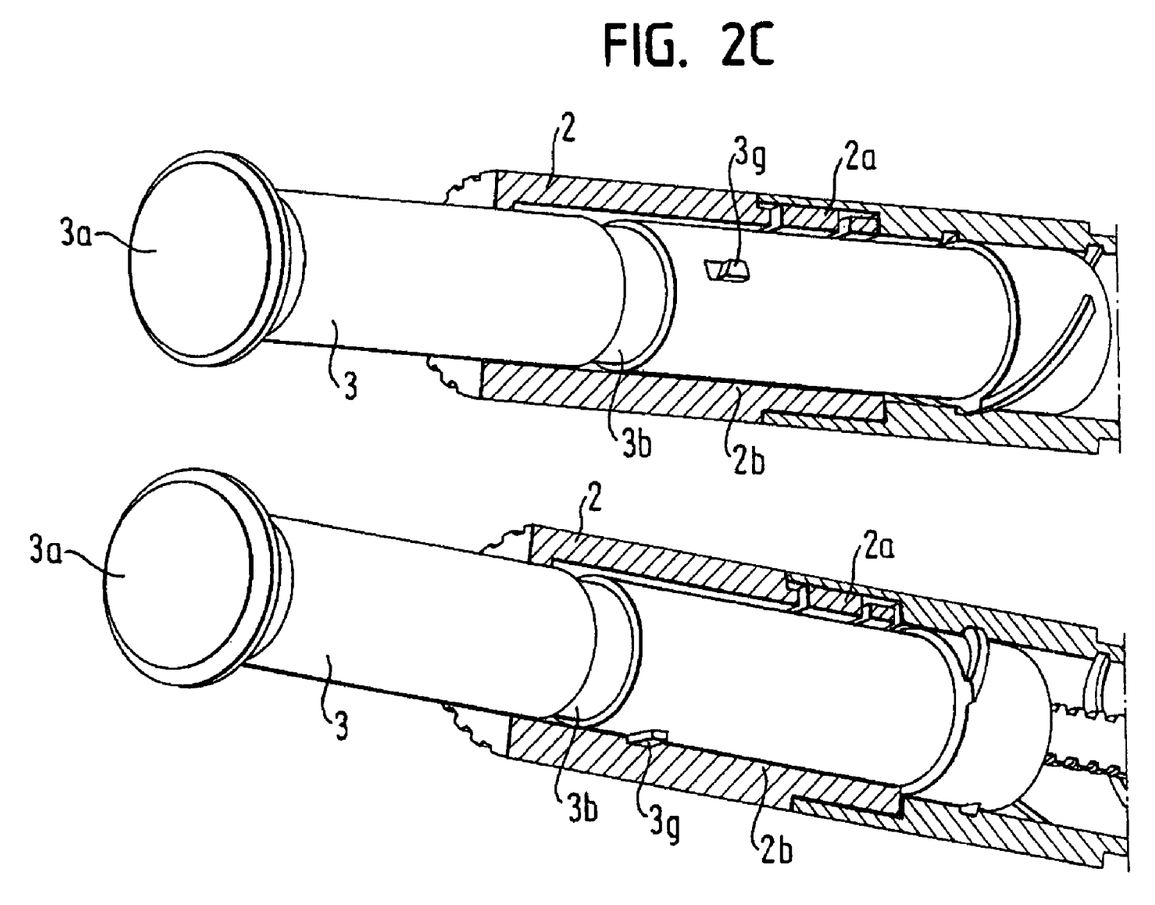

A stop strip 2b provided on the internal face of the setting sleeve 2, the radial position of which was fixed by the setting or rotating procedure of the setting sleeve 2, restricts a maximum possible rotating or priming movement of the rotating sleeve 3, which has a stop element 3g on its external face, for example in the form of a protruding cam. As illustrated in FIG. 2C, the rotating sleeve 3 can be rotated out of the injection device 1 until the stop element 3g lies in contact with the stop strip 2b of the setting sleeve and thus prevents the rotating sleeve 3 from being rotated or extracted any farther.

As may be seen from FIGS. 2B and 2C, as the rotating sleeve 3 is being extracted or extended during the priming process, the release groove 3b provided on the rotating sleeve 3 is moved away from the setting lock cam 2a of the setting sleeve 2 so that the setting lock cam 2a can no longer flex radially inwards and thus engage in the catch 1d provided on the internal face of the housing 1a, thereby preventing a radial or rotating movement of the setting sleeve 2 relative to the injection device 1 or the housing element 1a. The dose which can be set by means of the setting sleeve 2 can therefore no longer be changed during a priming and administering process when the rotating sleeve 3 is at least partially extracted.

In the interior of the rotating sleeve 3 during priming, the locking element 5 rotates into the rotating sleeve 3 and relative to it, i.e, the locking element is moved relative to the rotating sleeve 3 in the distal direction of the rotating sleeve 3, because the locking element is mounted on the threaded rod 4 so that it can not rotate and the rotating sleeve 3 is rotated relative to the locking element 5 as it is rotated out, which causes a relative movement of the locking element 5 in the axial direction of the rotating sleeve 3 due to the thread engagement of the locking element 5 in the internal thread 3d of the rotating sleeve 3.

During the process of priming the injection device, i.e. as the rotating sleeve 3 is rotated out, the front rotation-restricting element 6b connected to the injection device prevents the threaded rod 4 from rotating as the injection device is primed, whereas the rotation-restricting element 6a connected to the rotating sleeve 3 permits a rotating motion of the rotating sleeve 3 relative to the threaded rod 4 retained by the rotation-restricting element 6b.

Figure 2D:
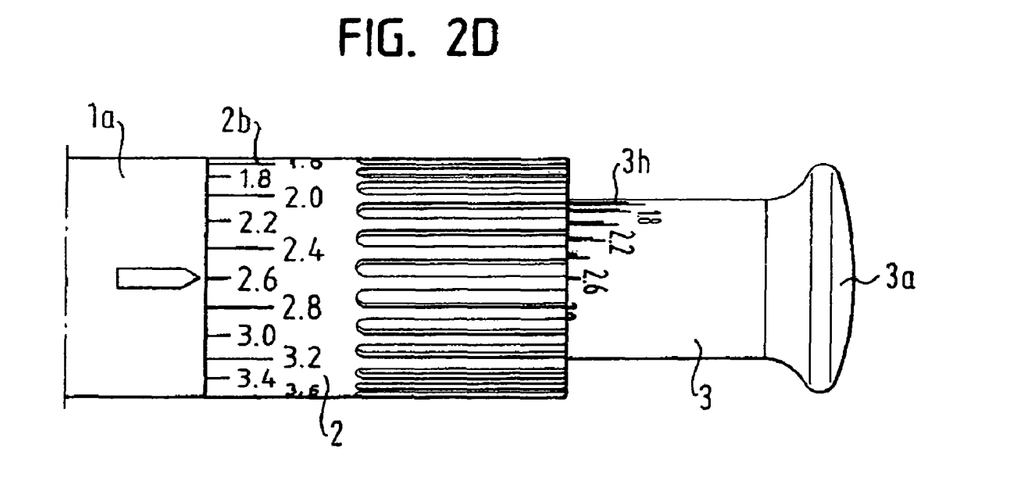

As illustrated in FIG. 2D, a mark, marking or indicator is provided in the circumferential direction on the internal face of the setting sleeve 2 and, based on the setting illustrated in FIG. 2D, a dose of 2.6 was set by turning the setting sleeve 2 so that a rotation position associated with the dose 2.6 marked by a dash lies alongside a marking element on the housing 1a indicated by an arrow. When the rotating sleeve 3 is in the fully extracted state, which is determined by the abutment of the stop element 3g on the stop strip 2b, the rotating sleeve 3 is rotated so far out of the injection device that a marking of the dose 2.6 actually primed, disposed on the circumferential face of the rotating sleeve 3, is fully visible, in which case the 2.6 marking on the rotating sleeve 3 lies in an axial extension of the 2.6 marking on the setting sleeve 2, thereby indicating to the user that the set dose has actually been primed. A user can compare the set dose with the primed dose by looking at the injection device, without having to check the set dose displayed on one side of the injection device against an "actually primed" dose displayed on the other side of the injection device, for example.

Figure 2E:
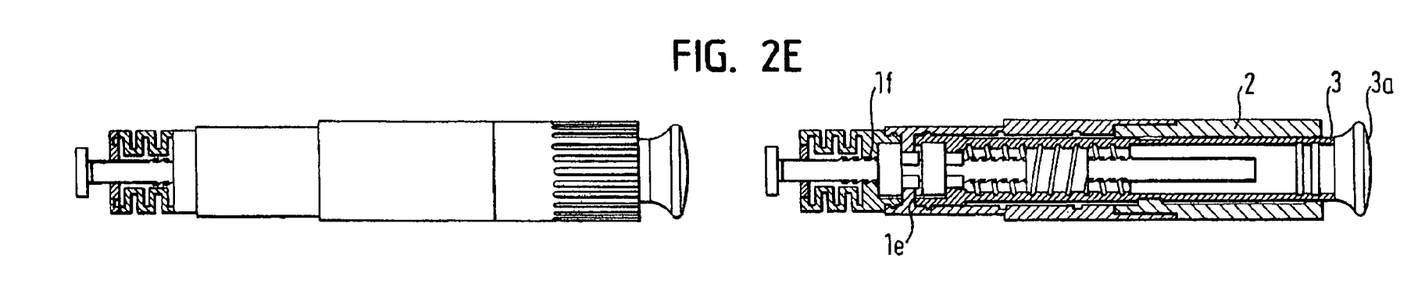

A pre-set dose can be dispensed by depressing the rotating knob 3*a*, as a result of which the rotating sleeve 3, which is mounted so as to rotate in the rotating knob 3*a*, is rotated in, as illustrated in FIG. 2E, until a front or distal end of the rotating sleeve 3 lies against an internal stop 1*e* of the injection device 1. As the rotating sleeve 3 is rotated in, the front rotation-restricting element 6*b* connected to the injection device 1 releases the rotating movement of the threaded rod 4, which is retained by the rotation-restricting element 6*a* connected to the rotating sleeve 3 and rotated together with the rotating sleeve 3 relative to the injection device 1 and is therefore screwed in the distal direction relative to the injection device 1 due to a thread engagement in an internal thread 1*f* of the injection device 1, in order to push a plug 7 lying against the front end of the threaded rod 4 for example, into an ampoule 8, as illustrated in FIG. 1B, and force out a substance contained in the ampoule 8 so that the pre-set dose is dispensed.

After dispensing, the dose set by means of the setting sleeve 2 can be primed again and dispensed by extracting the rotating sleeve 3 as described above, without having to set the dose again because the setting or rotation position of the setting sleeve 2 was not altered during the priming and dispensing process.

When the locking element 5 is inserted in the rotating sleeve 3 so that the total possible distance covered by the locking element 5 as far as a front stop inside the rotating sleeve 3 corresponds to a desired maximum quantity of substance to be dispensed, the process of priming the injection device can be limited by blocking the extraction of the rotating sleeve 3 if a dose set by means of the setting sleeve 2 is bigger than the pre-set maximum permissible total quantity which can be administered.

Figure 2F:
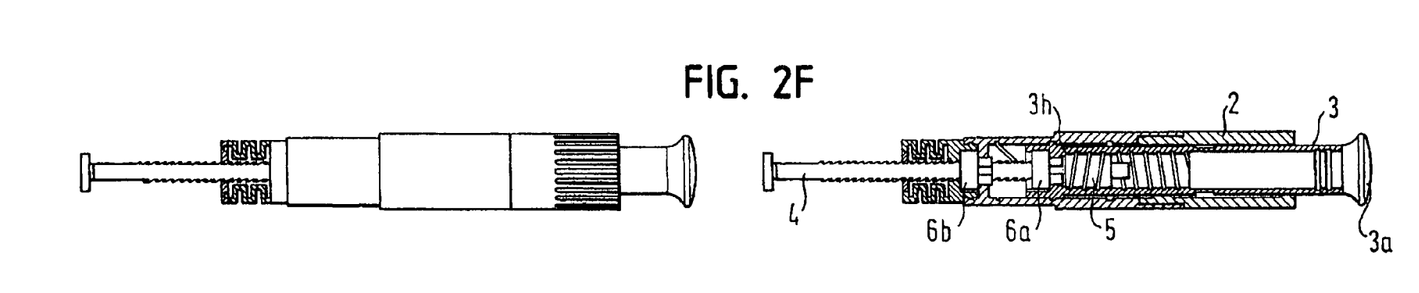

When a final permissible dose has been primed, as illustrated in FIG. 2F for example, the rotating sleeve 3 is pulled out or rotated out of the injection device 1 by means of the rotating knob 3*a* again. At the same time, the locking element 5 rotates in the interior of the rotating sleeve 3 until the locking element 5 lies against a front stop 3*h* of the rotating sleeve 3, thereby blocking any further outward rotation of the rotating sleeve 3, which is retained by the thread engagement with the external thread 5*a* of the locking element 5, which is not able to rotate relative to the injection device because it is mounted on the threaded rod 4 so that it cannot rotate, the latter being retained by means of the rotation-restricting element 6*b* connected to the injection device 1 so that it can not rotate during the extraction or priming process.

Figure 2G:
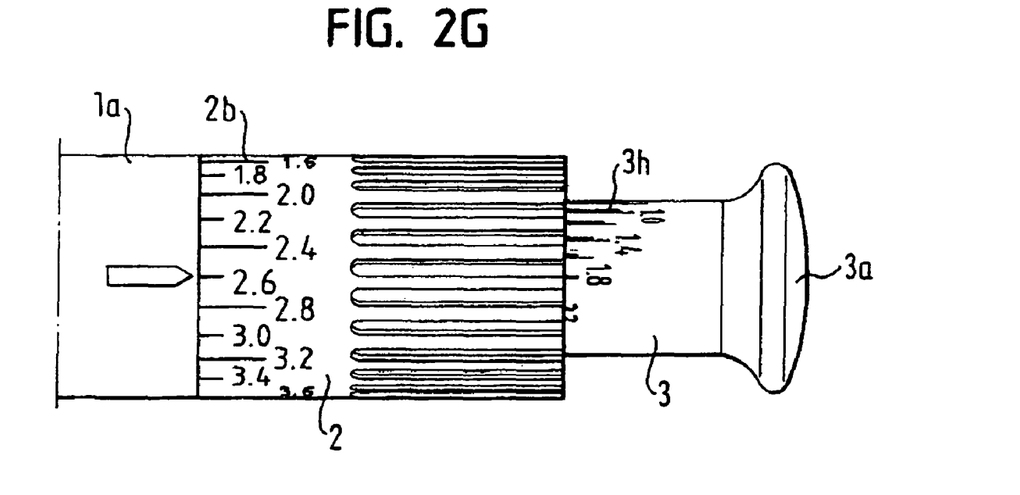

As illustrated in FIG. 2G, a user can easily see that, in the axial extension of the 2.6 marking provided on the setting sleeve 2, the maximum possible dose which is still possible is displayed as being 1.8 when the rotating sleeve 3 is in the locked, extracted end state, so that a user can easily tell that the desired set dose can no longer be administered.

Figure 2H:
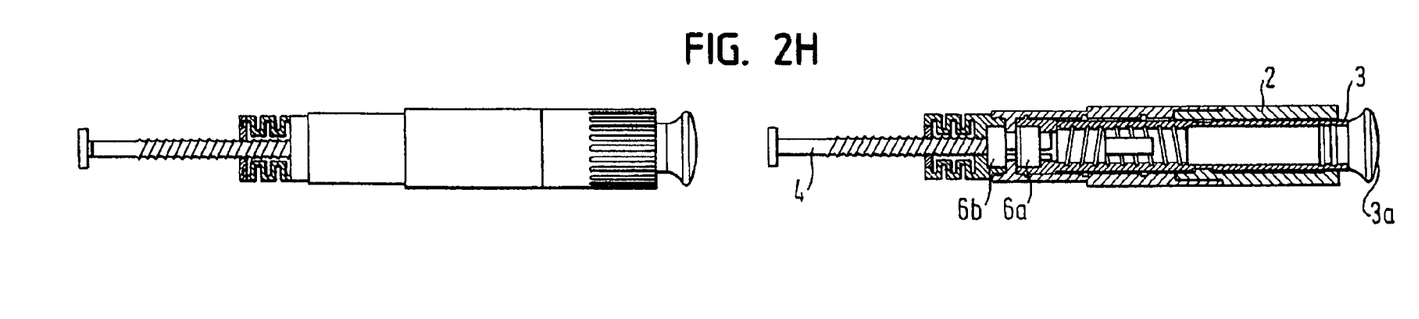

As illustrated in FIG. 2H, the final dose can be dispensed by depressing the rotating knob 3*a*. Due to the fact that the locking element 5 is completely screwed into the rotating sleeve 3 and is sitting against the front stop 3*h* of the rotating sleeve 3, the injection device cannot be primed again.

Due to the difference in the thread pitches of the external thread 4*b* of the threaded rod 4 and the external thread 3*c* of the rotating sleeve 3, for example the thread pitch of the external thread 3*c* of the rotating sleeve 3 is bigger than that of the external thread 4*b* of the threaded rod 4, a reduction ratio is achieved in the dispensing process. During priming, the rotating sleeve 3 is extracted farther out of the injection device 1 than the threaded rod 4 is displaced axially in the distal direction when the rotating sleeve 3 is pushed in because the rotating sleeve 3 is coupled in rotation with the threaded rod 4 during the pushing-in and dispensing process and the two elements therefore effect the same rotating motion. Since the external thread 3*c* of the rotating sleeve 3 has a bigger pitch than the external thread 4*b* of the threaded rod 4, a longer priming and pushing-in movement of the rotating sleeve 3 in the axial direction will mean that the forward movement of the threaded rod 4 in the axial direction will be shorter, which leads to a finer metering of the substance dispensed from the ampoule 8 by a forward movement of the threaded rod 4. Likewise, the ratio of the pitch of the external thread of the rotating sleeve 3 to that of the external thread of the threaded rod 4 can be fixed so that there is an increase in ratio or alternatively no increase or reduction in ratio.

Figure 3A:
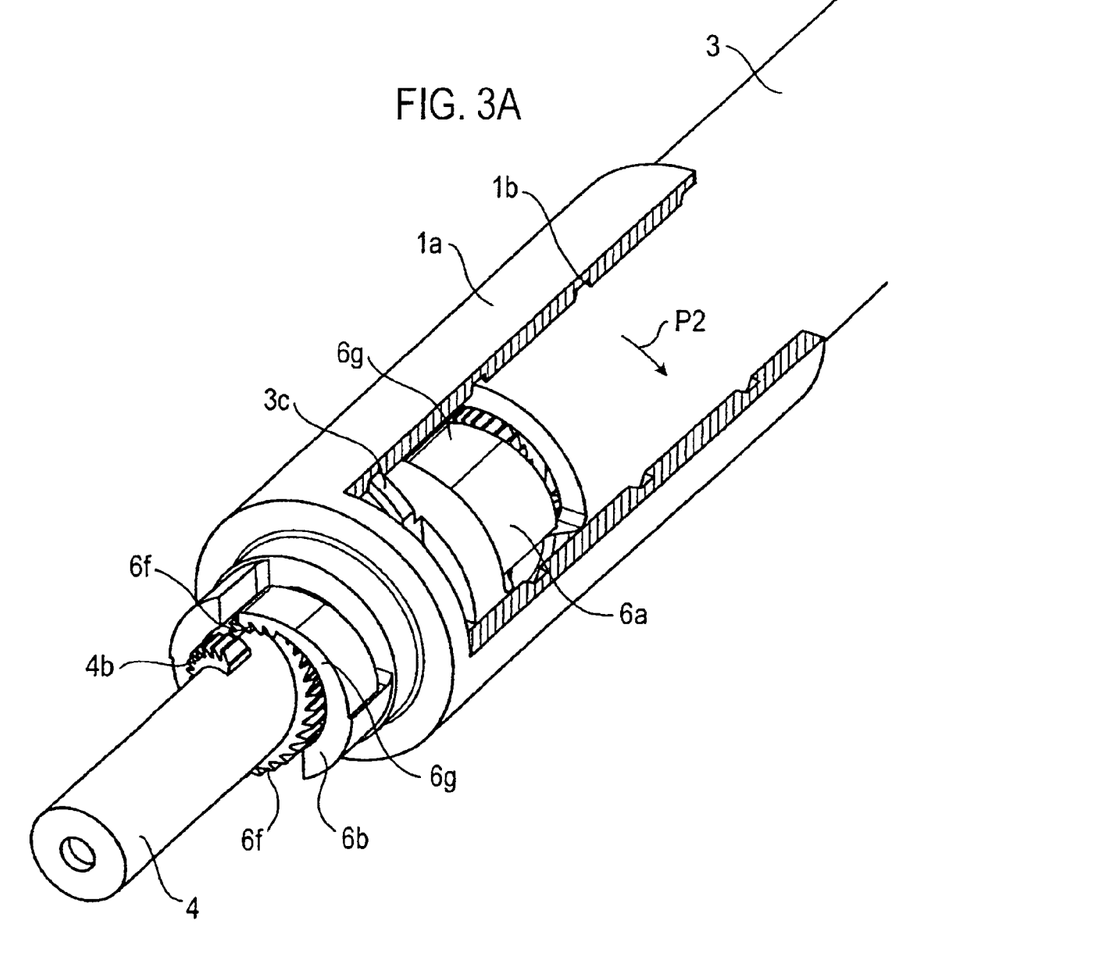
FIGS. 3A and 3B illustrate an embodiment of an anti-rotation lock in accordance with the present invention.
Figure 3B:
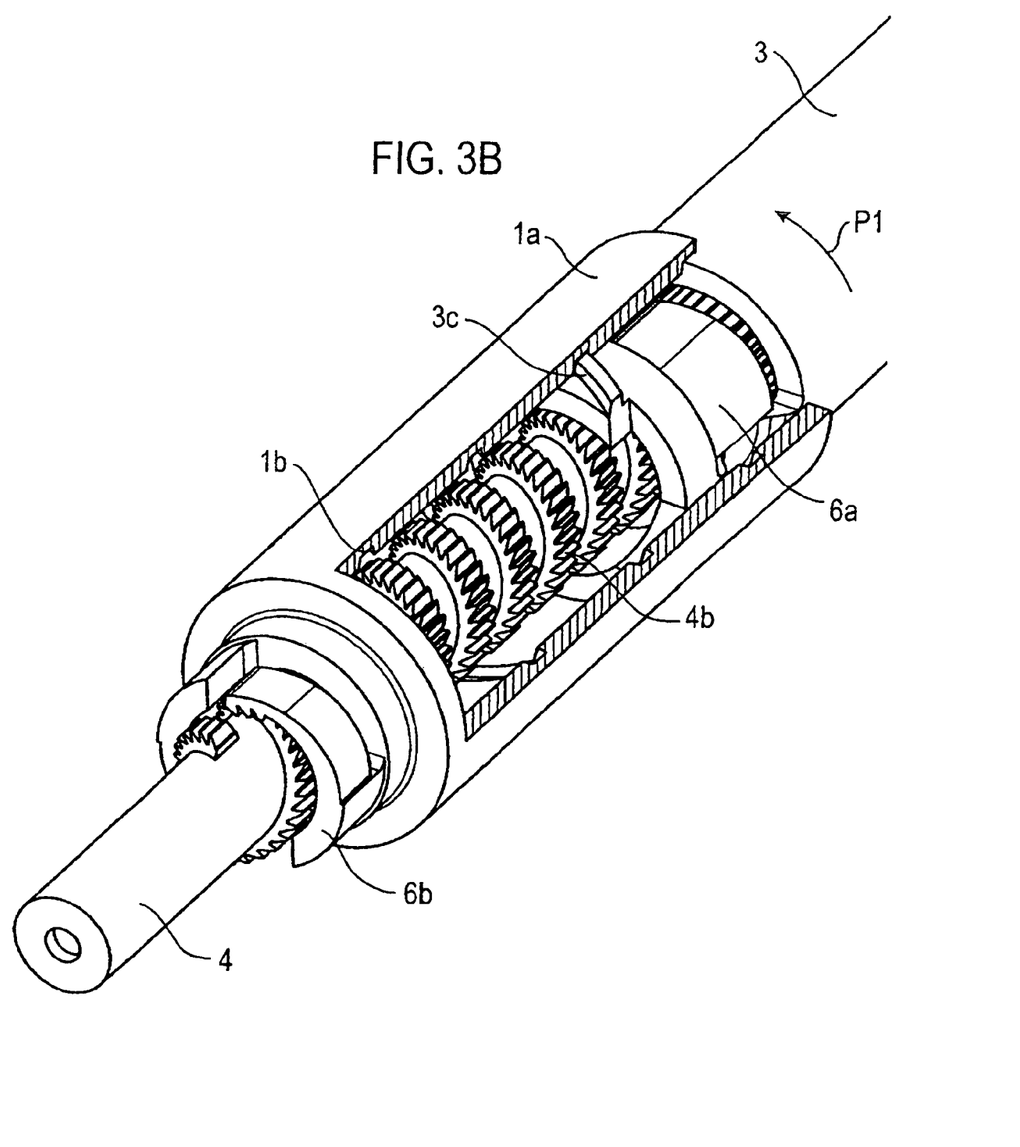

FIGS. 3A and 3B illustrate another embodiment of the rotation-restricting elements 6*a* and 6*b*. In the illustrated embodiment, the threaded rod 4 has a circumferential thread 4*b*, which has teeth in the circumferential direction, and the individual teeth are designed to permit a latching or retaining action on a tooth flank by means of matching, complementary teeth or a catch element, whereas the other tooth flank is designed to permit a sliding or displacement motion on a catch or complementary element. For example, the tooth flank providing an engagement or retaining effect may extend outwards essentially in the radial direction, whilst the tooth flank permitting a rotating or sliding motion is oblique or inclined at an angle relative to this tooth flank.

Permanently joined to or directly integrated in the injection device 1 or a housing part 1*a* is a rotation-restricting element 6*b*, which, in the embodiment illustrated, has two oppositely lying catch elements 6*f* formed by three tooth flanks which are mounted on elastic or catch arms. The thread 4*b* is guided inside the injection device 1 or the housing part 1*a* by means of an internal thread so that the threaded rod 4 is mounted so that it can rotate in the injection device 1 or the housing part 1*a* due to a thread engagement and can be screwed in or out of it. Due to the engagement of the catch elements 6*f* in the teeth provided on the thread 4*b* of the threaded rod 4, the threaded rod 4 is able to rotate relative to the housing part 1*a* in one direction only, whereas any movement in the opposite direction is blocked. In the embodiment illustrated in FIG. 3A, the threaded rod 4 can be rotated clockwise, which means that the threaded rod 4 can only be screwed out of the housing part 1*a* in the distal direction but cannot be screwed in the opposite direction.

The rotation-restricting element 6*a* which may be permanently joined to, integrated in, or associated with the rotating sleeve 3 is of the same construction as the rotation-restricting element 6*b* and also has catch elements 6*f* mounted on elastic arms 6*g* extending round the threaded rod 4 which are able to engage in the teeth of the thread 4*b* of the threaded rod 4 in order to permit a rotating motion between the threaded rod 4 and rotating sleeve 3 in one direction and block any rotating movement in the other direction, as described above.

FIG. 3A illustrates the rotating sleeve 3 fully rotated into the injection device, being guided by means of an external thread 3*c* in an internal thread 1*b* of the injection device housing 1*a*.

When the injection device 1 is primed by rotating out the rotating sleeve 3, the threaded rod 4 is locked by the rotation-restricting element 6b preventing it from rotating relative to the injection device housing 1a, whereas in the direction indicated by arrow P1 which causes the rotating sleeve 3 to rotate out of the housing 1a, the rotation-restricting element 6a is not in blocking engagement with the teeth on the thread 4b of the threaded rod 4.

When the rotating sleeve 3 is rotated again in the direction indicated by arrow P2 in FIG. 3A, the engaging elements of the rotation-restricting element 6a of the rotating sleeve 3 are engaged with the teeth of the thread 4a of the threaded rod 4, as a result of which the threaded rod 4 is coupled with the rotating sleeve 3 so that it can not rotate as the rotating sleeve 3 is being rotated inwards, and is driven and rotated with the latter. The rotation-restricting element 6b of the injection device allows the threaded rod 4 to rotate relative to the injection device 1 or the housing 1a so that the threaded rod 4 is rotated by the rotating sleeve 3 and guided in the internal thread of the injection device 1 or the injection housing 1a and is thus rotated out of the housing 1a in the distal direction in order to administer a set and primed dose. The injection device can then be primed again by rotating the rotating sleeve 3 out in the direction indicated by arrow P1 in FIG. 3B.

The embodiment of the rotation-restricting elements 6a and 6b illustrated in FIGS. 3A and 3B can be used in a dose metering mechanism or injection device instead of the rotation-restricting elements 6a and 6b described with reference to FIGS. 1 and 2, in which case all other elements of the injection device may remain the same. For example, the locking element 5 can be guided on the threaded rod 4 locked in rotation by providing one or more engaging elements in the axial direction on the internal face of the locking element 5, which can be guided in the teeth of the external thread 4b of the threaded rod 4, so that the locking element 5 is mounted so as to be axially displaceable but prevented from rotating on the threaded rod 4.

Figure 4A:
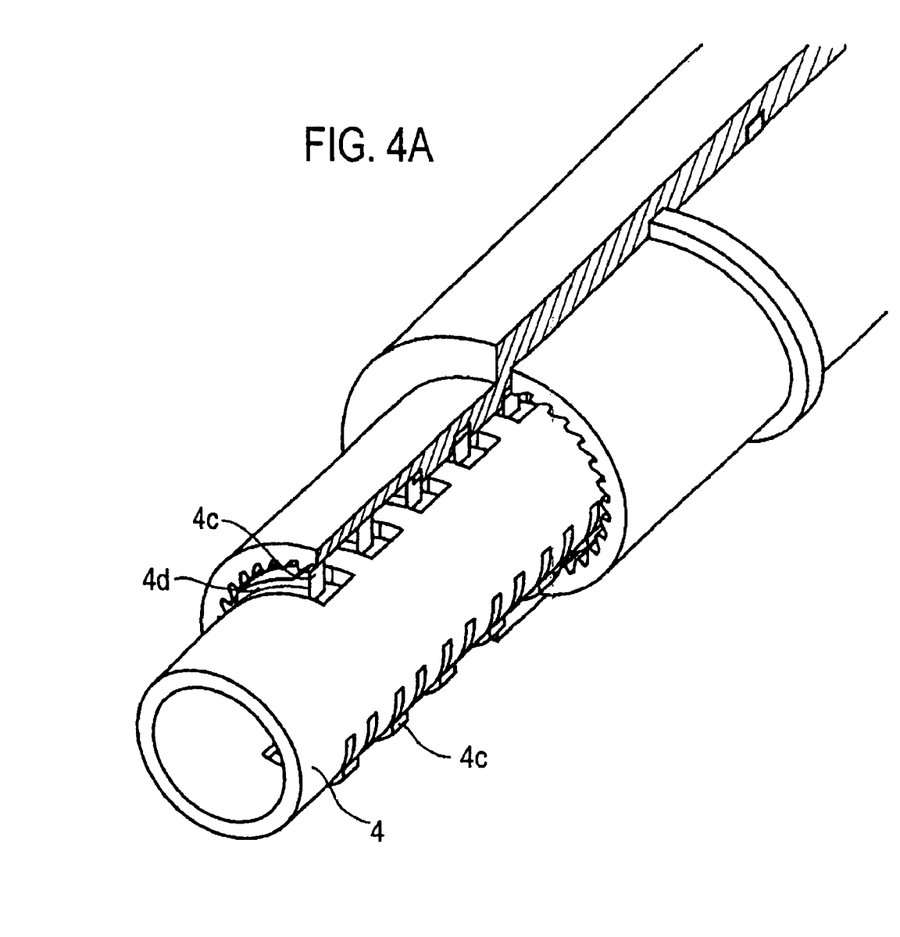
FIGS. 4A-4C illustrate another embodiment of an anti-rotation lock.
Figure 4B:
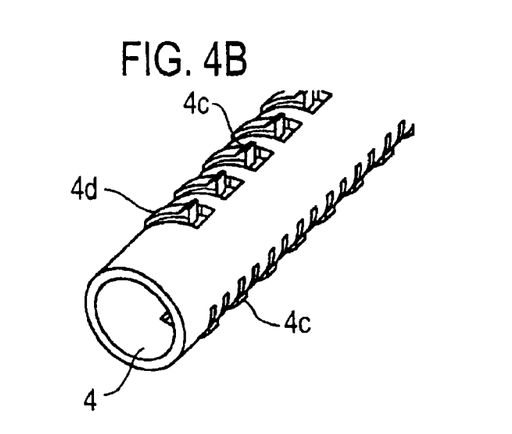
Figure 4C:
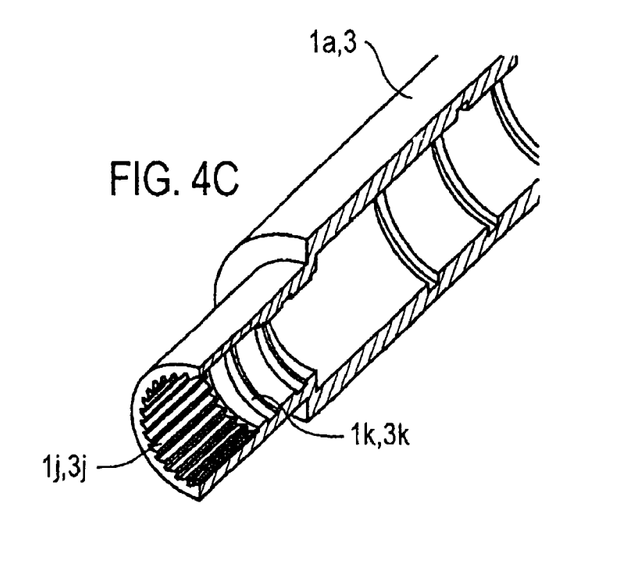

FIGS. 4A-4C illustrate another embodiment of a rotation-restricting element 6a or 6b, which may be integrated on a housing 1a of the injection device or on the rotating sleeve 3 or in these elements. This being the case, the operating mechanism is the reverse of that used for the embodiment described with reference to FIGS. 3A and 3B. The threaded rod 4 is provided with thread portion elements 4c, which are secured to the threaded rod 4 by means of elastic support arms 4d which are biased radially outwards, for example, and can engage in internal teeth 1j or 3j of the injection device housing 1a or the rotating sleeve 3. Provided on the internal face of the housing 1a or the rotating sleeve 3, axially offset from the catch or teeth 1j, 3j, is a thread or threaded portion 1k, 3k, in which the external thread of the threaded rod 4 formed by the catch elements 4c and support arms 4d can be guided.

The threaded rod 4 can therefore be rotated into the housing 1a or into the rotating sleeve 3, and the catch elements 4c of the threaded rod co-operating with the catch 1j, 3j permit a rotation of the threaded rod 4 relative to the housing 1a or relative to the rotating sleeve 3 in one direction only and lock any rotation in the opposite direction, as explained with reference to the embodiment illustrated in FIGS. 3A to 3B, for example.

In the same way as the rotation-restricting element 6a or 6b illustrated in FIGS. 3A and 3B, the embodiment illustrated in FIGS. 4A-4C may also be used in conjunction with the injection device or dose metering mechanism illustrated in FIGS. 1 and 2 instead of the rotation-restricting elements 6a an 6b specifically described in connection with them. In fact, any of the structures, features, steps or methods described herein may be used cooperatively.

The locking element 5 can be mounted so that it is prevented from rotating on the threaded rod 4 by providing a guide channel or groove on the internal face of the locking element 5 for example, in which the engaging or catch elements 4c can engage.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A dose metering mechanism for setting a dose to be administered from an injection device, the dose metering mechanism comprising:
   a setting sleeve marked with different dose amounts in the circumferential direction, by which setting sleeve a dose can be set by rotation, and
   a rotating sleeve configured to be axially displaced by rotation, said axial displacement relative to the setting sleeve to prime a dispensing of the set dose by rotation, said rotating sleeve marked with different dose amounts in the circumferential direction that match the dose amounts marked on the setting sleeve, wherein
   said setting sleeve is coupled to the rotating sleeve so that each time the rotating sleeve is fully rotated out, the set dose amount of the setting sleeve is not offset from an associated matching set dose amount of the rotating sleeve in the circumferential direction.

2. The dose metering mechanism as claimed in claim 1, wherein a dose to be administered is fixed by a position of rotation of the setting sleeve relative to the dose metering mechanism or to the injection device.

3. The dose metering mechanism as claimed in claim 1, wherein the position of rotation of the setting sleeve restricts the degree to which the rotating sleeve rotates out and defines a maximum possible angle of rotation of the rotating sleeve.

4. The dose metering mechanism as claimed in claim 3, wherein the position of rotation of the setting sleeve defines a maximum possible angle of rotation of the rotating sleeve.

5. The dose metering mechanism as claimed in claim 1, further comprising a locking element associated with the rotating sleeve which is moved toward an end stop associated with the rotating sleeve during every dose setting routine, and restricts the degree to which the rotating sleeve rotates out.

6. The dose metering mechanism as claimed in claim 1, wherein the setting sleeve is substantially coaxial with the rotating sleeve, and wherein the setting sleeve and the rotating sleeve each comprise a stop element which restricts the degree to which the rotating sleeve is able to rotate relative to the setting sleeve.

7. The dose metering mechanism as claimed in claim 1, wherein every dose amount on the setting sleeve is assigned a corresponding amount on the rotating sleeve.

8. The dose metering mechanism as claimed in claim 1, wherein the dose amounts on the rotating sleeve are offset from one another in an axial direction in rising sequence and in a spiral.

9. The dose metering mechanism as claimed in claim 1, further comprising a marking element associated with the injection device by which a reading is taken of the dose set by rotating the setting sleeve relative to the injection device.

10. An injection device comprising a dose metering mechanism for setting a dose to be administered from the injection device, the dose metering mechanism comprising:
   a setting sleeve marked with different dose amounts in the circumferential direction, by which setting sleeve a dose can be set by rotation,
   a rotating sleeve configured to be axially displaced in a proximal direction relative to the setting sleeve to prime a dispensing of the set dose by rotation in a first direction and further configured to be axially displaced in a distal direction relative to the setting sleeve to administer the set dose by rotation in a second direction, said rotating sleeve marked with different dose amounts in the circumferential direction, and
   a locking element having an external thread which is engaged with an internal thread of the rotating sleeve, wherein the locking element rotates into the rotating sleeve when the rotating sleeve is rotated out of the dose metering mechanism such that the locking element moves distally relative to the rotating sleeve toward a front stop of the rotating sleeve, wherein
   said setting sleeve is coupled to the rotating sleeve so that each time the rotating sleeve is fully rotated out, the set dose amount of the setting sleeve is not offset from an associated matching set dose amount of the rotating sleeve in the circumferential direction.

11. The injection device of claim 10, wherein the locking element restricts outward movement of the rotating sleeve if an available quantity of a substance to be administered is less than the set dose.

12. The injection device of claim 11, wherein the relative position between the locking element and the rotating sleeve is unchanged when the rotating sleeve is rotated into the dose metering mechanism to administer the set dose.

13. A dose metering mechanism for setting a dose to be administered from an injection device, said dose metering mechanism comprising a setting sleeve incorporating at least one marking with different dose amounts in a circumferential direction by which a dose to be administered can be set by rotation, a rotating sleeve configured to be axially displaced in a proximal direction relative to the setting sleeve to prime the dispensing of a dose by rotation in a first direction and further configured to be axially displaced in a distal direction relative to the setting sleeve to administer the set dose by rotation in a second direction, which rotating sleeve has at least one marking with different dose amounts in a circumferential direction that matches the dose amounts marked on the setting sleeve, and a locking element having an external thread which is engaged with an internal thread of the rotating sleeve, wherein the locking element rotates into the rotating sleeve when the rotating sleeve is rotated out of the dose metering mechanism such that the locking element moves distally relative to the rotating sleeve toward a front stop of the rotating sleeve, wherein the setting sleeve is coupled to the rotating sleeve so that each time the rotating sleeve is in a fully rotated out state, the set dose amount of the setting sleeve is not offset from an associated matching set dose amount of the rotating sleeve in the circumferential direction and wherein the setting sleeve is freely rotatable relative to the injection device when the rotating sleeve is in a fully pushed-in state and is rotably fixed when the rotating sleeve is moved from the fully pushed-in state.

14. The dose metering mechanism of claim 13, wherein the setting sleeve comprises one or more latching cams which lie opposite a circumferentially extending groove of the rotating sleeve when the rotating sleeve is in the fully pushed-in state.

15. The dose metering mechanism of claim 14, wherein the locking element restricts outward movement of the rotating sleeve if an available quantity of a substance to be administered is less than the set dose.

16. The dose metering mechanism of claim 15, wherein the relative position between the locking element and the rotating sleeve is unchanged when the rotating sleeve is rotated into the dose metering mechanism to administer the set dose.

* * * * *